US012254677B2

(12) United States Patent
Toporek et al.

(10) Patent No.: US 12,254,677 B2
(45) Date of Patent: Mar. 18, 2025

(54) SYSTEM AND METHODS FOR AUGMENTING X-RAY IMAGES FOR TRAINING OF DEEP NEURAL NETWORKS

(71) Applicant: KONINKLIJKE PHILIPS N.V., Eindhoven (NL)

(72) Inventors: Grzegorz Andrzej Toporek, Cambridge, MA (US); Ashish Sattyavrat Panse, Burlington, MA (US); Sean Kyne, Brookline, MA (US); Molly Lara Flexman, Melrose, MA (US); Jochen Kruecker, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 421 days.

(21) Appl. No.: 17/559,472

(22) Filed: Dec. 22, 2021

(65) Prior Publication Data
US 2022/0198784 A1 Jun. 23, 2022

Related U.S. Application Data

(60) Provisional application No. 63/129,670, filed on Dec. 23, 2020.

(30) Foreign Application Priority Data

Jan. 29, 2021 (EP) .................................... 21154325

(51) Int. Cl.
*G06V 10/77* (2022.01)
*G06T 7/00* (2017.01)
*G06V 10/774* (2022.01)

(52) U.S. Cl.
CPC ........ *G06V 10/7747* (2022.01); *G06T 7/0012* (2013.01); *G06T 2207/10116* (2013.01)

(58) Field of Classification Search
CPC ............ G06V 10/7747; G06V 2201/03; G06T 7/0012; G06T 2207/10116; G06T 5/60;
(Continued)

(56) References Cited

U.S. PATENT DOCUMENTS 10,282,588 B2  5/2019  Comaniciu
10,849,585 B1  12/2020  Teixeira
(Continued)

FOREIGN PATENT DOCUMENTS

WO   2019211131 A1   11/2019

OTHER PUBLICATIONS

Vidal, Franck et al "Development and Validation of Real-Time Simulation of X-Ray Imaging with Respiratory Motion", 2016.
(Continued)

*Primary Examiner* — Md K Talukder

(57) ABSTRACT

A training data modification system (TDM) for machine learning and related methods. The system comprises a data modifier (DM) configured to perform a modification operation to modify medical training X-ray imagery of a patient. The modification operation causes image structures in the modified medical training imagery. The image structure is representative of a property of i) a medical procedure, ii) an image acquisition operation by an X-ray-based medical imaging apparatus (IA), iii) an anatomy of the patient.

20 Claims, 7 Drawing Sheets

(58) Field of Classification Search
CPC . G06T 2207/20081; G06T 2207/20084; G06T 2207/30004; A61B 34/20; A61B 2034/102; A61B 2034/105; A61B 2090/376; A61B 5/7267; G06N 3/045; G06N 3/08

See application file for complete search history.

(56) References Cited

U.S. PATENT DOCUMENTS

| | | | | |
|---|---|---|---|---|
| 2018/0315188 | A1* | 11/2018 | Tegzes | G06T 7/11 |
| 2019/0139641 | A1* | 5/2019 | Itu | G06N 3/045 |
| 2020/0315587 | A1 | 10/2020 | Toporek | |
| 2022/0044440 | A1* | 2/2022 | Blau | G06T 7/12 |
| 2022/0198784 | A1* | 6/2022 | Toporek | G06V 10/7747 |
| 2023/0020252 | A1* | 1/2023 | Kruecker | A61B 6/5211 |
| 2023/0146953 | A1* | 5/2023 | Park | G06T 7/0012 382/131 |
| 2023/0260172 | A1* | 8/2023 | Koehler | G06T 11/006 382/100 |

OTHER PUBLICATIONS

Deng, Luzhen et al "A Geant4-based Monte Carlo study of a benchtop multi-pinhole X-ray fluorescence computed tomography imaging", International Journal of Nanomedicine, vol. Nov 8;13, pp. 7207-7216 (2018).

Bonifacio, Daniel A. B. et al , "Monte Carlo simulation of X-ray spectra in diagnostic radiology and mammography using Geant4", published as a conference paper, "International Nuclear Atlantic Conference—INAC 2005", Santos, SP, Brazil, Aug. 28 to Sep. 2, 2005, Associação Brasileira de Energia Nuclear (ABEN), ISBN: 85-99141-01-5.

Alvarez, Robert E. et al "Energy-selective reconstructions in X-ray computerized tomography", Physics in Medicine and Biology, vol. 21, No. 5, pp. 733-744. 1976.

Goodfellow, Ian J. et al GANs ("Generative Adversarial Nets"), in 2014 (available online at arXiv:1406.266).

Heimann, Tobias et al "Real-Time Ultrasound Transducer Localization in Fluoroscopy Images by Transfer Leaning from Synthetic Training Data", Medical Image Analysis, 2014.

Bowles, Christopher et at "GANsfer Learning: Combining labelled and unlabelled data for GAN based data augmentation", 2018.

Wang, Xiaosong et al."ChestX-ray8: Hospital-scale Chest X-ray Database and Benchmarks on Weakly-Supervised Classification and Localization of Common Thorax Diseases" 2017, arXiv:170502315v5.

Tekchandani, Hitesh et al, "Mediastinal lymph node malignancy detection in computed tomography images using fully convolutional network", Biocybernetics and Biomedical Engineering, vol. 40, 2020, pp. 187-199.

Cha, Kenny et al "Reducing overfitting of a deep learning breast mass detection algorithm in mammography using synthetic images", Proceedings of SPIE, Medical Imaging, 2019.

Madani, Ali et al "Chest x-ray generation and data augmentation for cardiovascular abnormality classification", Proceedings of SPIE, Medical Imaging, 2018.

\* cited by examiner

SYSTEM AND METHODS FOR AUGMENTING X-RAY IMAGES FOR TRAINING OF DEEP NEURAL NETWORKS

FIELD OF THE INVENTION

The invention relates to a training data modification system, to one or more computer memories, to a system for processing medical imagery, to a method of modifying training data for machine learning, to a method of training a machine learning model for processing medical imagery, method for processing medical imagery, to a computer program element, and to computer readable medium.

BACKGROUND OF THE INVENTION

Training of a machine learning model, in particular those of sufficient complexity such as artificial neural networks having a large number of parameters, may lead to overfitting. Overfitting occurs when the machine learning model simply memorizes provided training data, rather than generalizes well to new examples. Overfitting can be overcome by providing more training data. However, assembling a sufficiently large set of labelled clinical training cases (especially with devices/instruments represented in the images) is either not feasible at all, or laborious and expensive.

Another reason for poor generalizations of certain machine learning models, in particular those with a so called deep architecture, is a possible bias that may exist in a given training dataset. For instance, training cases including labelled X-ray images may be biased against certain patient population subgroups as well as certain conditions. More specifically, suppose patients with pneumothorax from a given dataset always underwent chest drain procedures. As an unintended side effect of this, the machine learning model may erroneously learn to identify chest drain tubes in the imagery, rather than to learn what is wanted, for example to learn identifying certain medical condition. Bias in training data may thus lead to significant prediction inaccuracies due to the construction by the model of spurious correlations.

SUMMARY OF THE INVENTION

There may therefore be a need for improving the performance of machine learning, in particular in relation to machine learning based on X-ray imagery.

An object of the present invention is achieved by the subject matter of the independent claims where further embodiments are incorporated in the dependent claims. It should be noted that the following described aspect of the invention equally applies to the one or more computer memories, to the system for processing medical imagery, to the method of modifying training data for machine learning, to the method of training the machine learning model for processing medical imagery, to the method for processing medical imagery, to the computer program element and to the computer readable medium.

According to a first aspect of the invention there is provided a training data modification system for machine learning, comprising:

a data modifier configured to perform a modification operation to modify medical training X-ray imagery of one or more patients, the modification operation causing one or more image structures in the modified medical training imagery, the said one or more image structure representative of at least one property of i) a medical procedure, ii) an image acquisition operation by an X-ray-based medical imaging apparatus, iii) an anatomy of the one or more patient.

The modification may include adding or removing of image structure/image feature. The modification may also include simulation of X-ray properties. The modification operation may be local or global.

The medical procedure may in particular require presence of one or more medical tools/device/equipment during imaging, at least at times, in the field of view of the imaging apparatus.

The image acquisition operation may require any one or more of filter setting, magnification setting, imaging geometry setting, tube voltage/amperage setting, or any other setting that affects image contrast mechanism of the imaging apparatus. The settings may be as required in an imaging protocol.

In embodiments, the modification operation includes projecting a projection footprint into the medical imagery of i) a model of a medical tool for the medical procedure, and/or of ii) a model of an equipment of the imaging apparatus, and/or of iii) a model of an anatomy or part thereof.

The said equipment may include filter or collimator blades, etc, or any other part of the imaging apparatus that may reside in the FOV, at least in parts and at times.

The said model may be a CAD (computer-aided-design) or mesh model stored in a computer memory. The model may represent any one or more of: shape, position or state (deformation) of a medical tool/device/equipment required in an imaging procure and at times resides in a field of view of the imaging apparatus. The said tool/device/equipment may include guidewires, guiding catheters, etc. The model may also relate to an anatomical structure (vessel mesh), bone deformation, etc.

In embodiments, the image acquisition operation is determined by one or more imaging parameters for X-radiation generatable by the imaging apparatus, wherein the one or more image structures caused by the data modifier relates to the said generatable X-radiation.

The imaging parameter may include any one or more of magnification, detector gain, voltage/amperage in relation to an X-ray source. The magnification is determined by the distance between detector and X-ray source.

In embodiments, the modification operation is randomized or deterministic.

The randomization can be implemented by a random number generator. In particular, the selection of which image is to be modified may be randomized. In addition or instead, how the modification is to be applied may be randomized. Specifically, for a local modification, it is randomized where the modification is to be applied in the image.

In embodiments, the modification operation is constrained by prior anatomical knowledge that pertains to the one or more patient. In particular, the modification may still be randomized, but is so constrained.

In embodiments, the modification operation is constrained by temporal constraints that pertain to the one or more patients and/or the medical procedure. For example, only possible positions and/or speed of a device/tool/equipment, given an earlier position, are considered when formulating the modification operation.

In another aspect there is provided a system for training a machine learning model for processing medical imagery, configured to adjust one or more parameters of the machine learning model based at least on the modified medical training imagery as provided by the system of any one of the above described embodiments.

Preferably, in training, the modified image(s) are used together with the original, non-modified training images. During training, a random selection is made so that either a modified or an original non-modified training image is used/drawn. For example, during a given training iteration, a subset ("(mini-)batch") of training images is used, that may comprise a mix of modified and original non-modified training images.

In another aspect there is provided one or more volatile or non-volatile computer memory on which is stored the machine learning model so trained by the system and/or on which is stored at least some of the modified medical imagery generated by a training data modification system of any one of the above described embodiments.

In another aspect there is provided a system for processing medical imagery, comprising:
an input interface for receiving medical imagery obtained by a medical imaging apparatus;
the trained machine learning model; and
the system configured to apply the input medical imagery to the trained machine learning model, to obtain a medical machine learning result.

Alternatively, no such model is used, but the input medical imagery is applied to an enlarged data set including the modified data and the original data, to obtain the result, such as when using a clustering algorithm, such as a k-nearest neighbor clustering algorithm, or other types of non-model based machine learning algorithms.

The result may include any one or more of regression or classification result. The result may include any one of: clustering, forecasting, data generation (e.g. image reconstruction, future sentence given a previous sentence, or language translation), dimensionality reduction, unsupervised feature learning, segmentation.

In another aspect there is provided a method of modifying training data for machine learning, comprising modifying medical training X-ray imagery of one or more patients, the said modifying causing one or more image structures in the modified medical training imagery, the said one or more image structure representative of at least one property of i) a medical procedure, ii) an image acquisition operation by an X-ray-based medical imaging apparatus, iii) an anatomy of the one or more patient.

In another aspect there is provided a method of training a machine learning model for processing medical imagery, based at least on the modified medical training imagery as obtained by the method of modifying training data.

In another aspect there is provided a method for processing medical imagery, comprising applying input medical imagery to the modified training data or to the said trained machine learning model, to obtain a medical machine learning result.

The proposed systems and method implements a type of data augmentation or preparation—a synthetic creation of new training dataset, based on an existing training dataset. The newly created training data/cases may be considered a type of data-driven regularization in machine learning that reduces generalization error. The proposed systems and method implement a new type of data augmentation, geared towards X-ray image based training data sets.

The proposed system and method allow enlarging an existing training data set to obtain a higher statistical variability in the so enlarged training set. So enlarging the set allows for compensating for an existing bias in the existing (original) data set. In particular, a risk of constructing spurious correlation by machine learning algorithms/models can be reduced. In embodiments, the training data modification facilitates combination of priori knowledge on interventional devices (such as guidewires, balloons, stent retrievers) with an existing set of training x-ray image specimens, so as to reduce overfitting risks. The said prior knowledge may include knowledge of shape, configuration, mechanical properties, characteristics, etc of such devices that may reside in the field of view during X-ray imaging.

The proposed system and method is particularly suited to improve training data sets for machine learning that include X-ray projection imagery, as such imagery poses unique challenges. The said challenges relate to the manner in which information is recorded in X-ray projection imagery. In X-ray projection imagery, separate objects in 3D overlap in projection view and/or fore- and background information is merged. In addition, projection footprints in the image plane of the very same object in 3D varies with projection direction.

The system and method may also facilitate automated labeling/annotation to reduce costs and efforts in procuring training data. The system and methods implement a training data augmentation protocol.

In another aspect there is provided a computer program element, which, when being executed by at least one processing unit, is adapted to cause the processing unit to perform the method as per any one of the above mentioned embodiments.

In another aspect still, there is provided a computer readable medium having stored thereon the program element.

Definitions

"user" relates to a person, such as medical personnel or other, operating the imaging apparatus or overseeing the imaging procedure. In other words, the user is in general not the patient.

In general, the term "machine learning" includes a computerized arrangement (or module) that implements a machine learning ("ML") algorithm. Some such ML algorithms operate to adapt a machine learning model that is configured to perform a task. This adaption is called "training". Task performance by the ML model improves measurably, the more (new) training data is used or is used to train the model. The performance may be measured by objective tests when feeding the system with test data. The performance may be defined in terms of a certain error rate to be achieved for the given test data. See for example, T. M. Mitchell, *Machine Learning*", page 2, section 1.1, McGraw-Hill, 1997.

BRIEF DESCRIPTION OF THE DRAWINGS

Exemplary embodiments of the invention will now be described with reference to the following drawings, which, unless stated otherwise, are not to scale, wherein.

DETAILED DESCRIPTION OF EMBODIMENTS

Figures 1, 2:
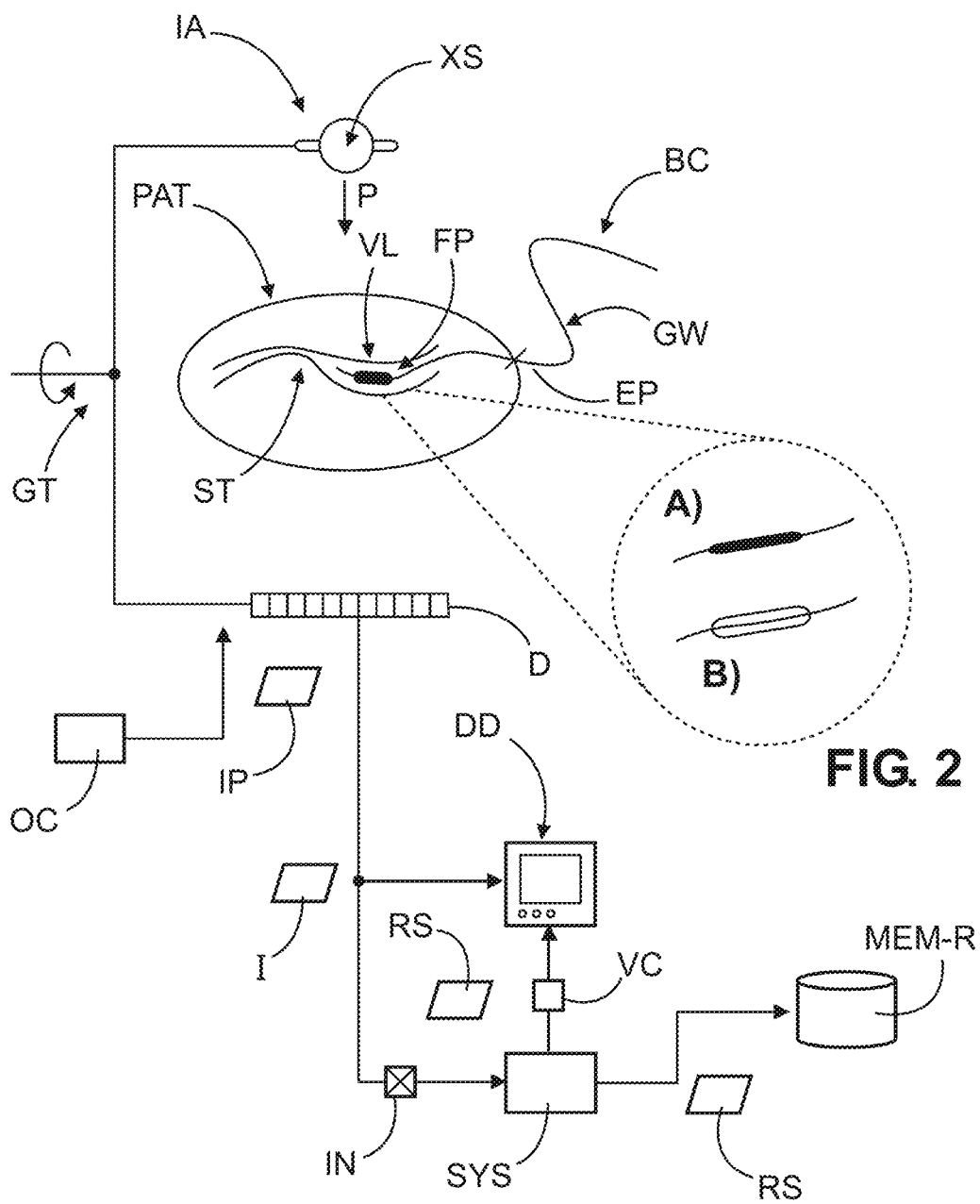
FIG. 1 shows a schematic block diagram of an imaging arrangement including an imaging apparatus and a computer system to process imagery acquired by the imaging apparatus.
FIG. 2 shows a close-up of a medical tool capable of assuming at least two states.

With reference to FIG. 1, this shows a block diagram of an arrangement that may be used to support a medical intervention or other medical procedure. The arrangement includes an imaging apparatus IA (sometimes referred to herein as "the imager") and a computer-implemented system SYS.

The supported intervention may be one of treating a stenosis in a human or animal patient using a medical tool or implement such as a balloon catheter CB. Other catheter types, or other medical interventions or procedures in which different tools are used are also envisaged herein, such a mitral valve repair procedures, etc.

The imaging apparatus is preferably an X-ray imaging apparatus that produces a single ray exposure, such as in radiography, or, as in fluoroscopy or angiography applications, a sequence of X-ray exposures referred to herein as frames or images. The imagery produced by the imager IA may be processed, possibly alongside other input, by the computer system SYS to compute a medical result RS to assist a medical user, such as an interventional cardiologist, in performing the intervention. Direct support by the computer system SYS during the intervention is envisaged herein, but the computer system SYS may also be used instead pre-intervention or post-intervention. For example, the system SYS may be used to prepare or plan an intervention or may be used to analyze data, such as imagery generated during previous one or more interventions to plan or inform follow-up treatments, interventions or other measures. Thus, the computer system may be a standalone system, not necessarily coupled to any imaging apparatus, and the processed imagery may not necessarily be live imagery but may instead be historic imagery, retrieved from an image database or other storage.

Figure 3:
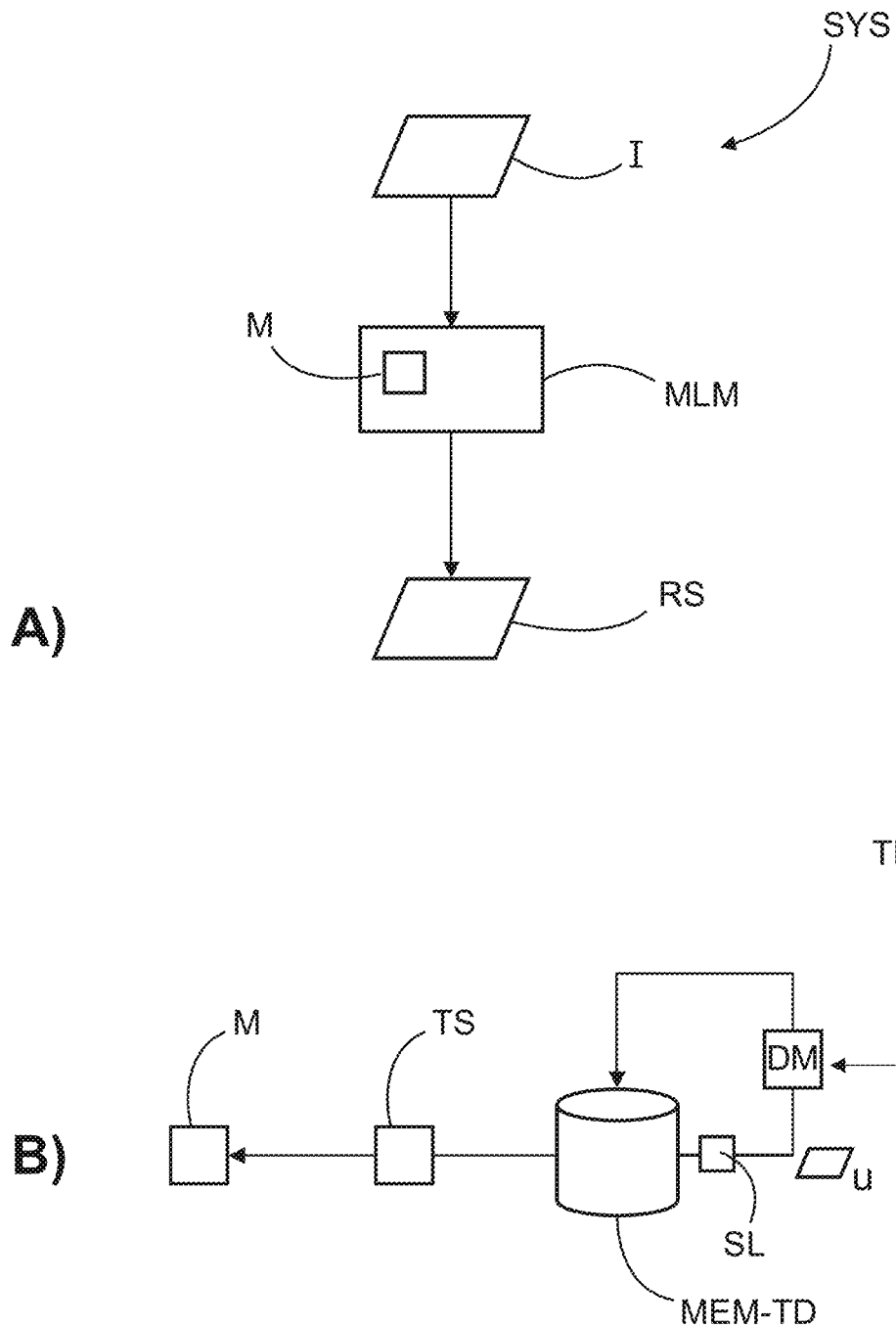
FIG. 3A, B shows a block diagram of the computer system used in FIG. 1 including a machine learning module.

As briefly mentioned, the system SYS processes the imagery and produces as output a medical result RS. This is shown in the block diagram of FIG. 3A. The system SYS preferably uses a machine learning module MLM that uses or used a set of training data. Specifically and in some embodiments, the machine learning module MLM includes a machine learning model M that has been pre-trained on the training data. The training data includes training imagery. The training data may have been generated in historical interventions or on other occasions, and may be held in medical data repositories such as a PACS (Picture Archive Communication System), HIS (Hospital Information System), patient health records, and so on.

Once trained, the MLM module can be used in deployment, such as in day-to-day clinical practice. The result RS produced by ML module MLM in deployment may be in text or image form, or in any other data type form, or in a combination thereof. The result RS produced by the machine learning based system SYS is to provide the user with information that can be gained from the imagery. As mentioned, in embodiments, in addition to the imagery, other (contextual) data may be co-processed with the imagery to arrive at the result RS. The result may be one of regression, or classification or any other, such as clustering, text generation. For example, the output result RS may be one of a diagnosis. Specifically, based on an image of a patient acquired by the (or other) imaging apparatus IA, a diagnosis is computed in respect of the patient. For example, a lesion is classified as benign or malign, etc. In other applications, the machine learning based system may analyze the acquired input imagery I to locate a position of the medical device or tool BC used in the intervention, such as a balloon catheter, guide wire GW or any other. This may assist navigation or provide other support to the user. Image-based recognition of individual organs, anatomies or parts thereof are examples of other such medical results RS envisaged herein.

In other words, the image arrangement not only provides image-guided support by way of the imagery produced by the imaging apparatus, but also adds value in providing additional information extracted from the imagery that may not be easily discernable by a human user. The medical user may inexperienced or may be in a situation of high stress as often happens in an operating theatre or a trauma room in a busy clinic for example.

Before explaining the machine learning based system SYS in more detail, some exemplary scenarios, in particular medical interventions, will be described in more detail to better illustrate operation of the proposed system SYS.

Turning now first to the imaging apparatus IA, this is preferably of the X-ray type and is configured to acquire X-ray projection image(s). The image may be a single still image, such a may be acquired in radiography, or may be part of a stream of images ("frames") that is used to display a video feed such as in fluoroscopy. The still image or stream may be displayed on a display device DD.

The imaging apparatus IA includes an X-ray source XS and an X-ray sensitive detector D. The imaging apparatus IA preferably allows acquiring imagery from different projection directions d. The imaging apparatus may include an optional gantry GT to which the X-ray source XS and/or the detector D are connected. The projection imagery may be acquired along different projection directions by rotation of the gantry (and with it, of the source XS and detector D) around the lesioned site ST or ROI. Such gantry-based imaging apparatuses include C- or U-arm systems and are mainly envisaged herein, but so are (CT) computed tomography scanners. Non-gantry based imaging solutions are also envisaged, such as mobile or portable imaging devices, where there is no, or no permanent, physical connection between detector D and radiation source XS. The imagery I to be processed by the system SYS may be projection imagery in projection domain as recorded by the detector D, or may comprise reconstructed imagery in image domain obtained by a computed tomography algorithm.

In more detail, during imaging, the X-ray source XS emits an X-ray beam which propagates along projection direction d to interact with patient tissue and/or the balloon catheter or other medical device BC, to cause a modified X-ray beam to emerge at the far end of the patient, and be detected at detector D. Data acquisition circuitry (not shown) of the detector D converts the received modified radiation into a set of numbers ("pixel values"), preferably stored in a respective matrix per frame/image, with respective rows and columns. The rows and columns define a size of the image/frame. The pixel values represent detected intensities. The pixel values per frame/image can be used by a visualization component VC to effect display of the image on the display device DD during the intervention. In the following we will no longer distinguish between frame and still image, and simply use the term "image/imagery" as a generic reference to both.

One type of medical interventions that uses medical devices resident in the imager's field of view (FOV), at least at times, is treatment of cardiac stenosis, or balloon angioplasty, also known as percutaneous transluminal angioplasty (PTA). The FOV is the portion of space that is being imaged by the imaging apparatus. The stenosis may be treated by advancing a distal portion of the balloon catheter BC through the patient to the lesioned site such as the structured site ST, a portion of a lesioned blood vessel. A guide wire GW may be used to navigate and push the catheter's distal treatment portion to the site ST. A range of different types of balloon catheters are envisaged herein including those of the over-the-wire (OTW) type or rapid exchange (RX) type, or others still. In general, balloon catheters BC include a tube with the said distal end, and a proximal end. The proximal end remains outside the patient with a user, such as an interventional cardiologist, so that the user can control the operation of the catheter. The distal portion is introduced into the patient through an entry point EP, such as at the femoral artery or vein, and is advanced through the vasculature to the lesioned site ST. The distal portion of the catheter tube in balloon catheters is formed into a balloon portion FP that is inflatable with liquid such as water or preferably a saline solution. The liquid is administered through a port portion at the proximal end to inflate the balloon portion FP. Upon removal of some or all of the liquid, the balloon deflates. The balloon portion FP is formed from an elastic material such as an elastomer with suitable elasticity properties. The balloon portion FP is advanced by user of the guide wire via the entry point EP to the lesioned site and during operation of the image apparatus IA to assist navigation through the vasculature. Upon arrival at the lesioned site ST, the balloon portion FP may be inflated by introduction of the liquid into the balloon FP, thus causing a force on the vessel VL walls to be exerted to so broaden the stricture thus treating same. FIGS. 2A, B are close-ups that show respectively two states of the balloon portion FP of the balloon catheter BC. FIG. 2A shows the deflated state of the balloon portion which can be ascertained as the slightly thickened part (shown in black) of the distal portion of the balloon catheter, whilst FIG. 2B shows an inflated state of the balloon portion FP. Other medical procedures or interventions may call for other medical devices, such as in transcatheter aortic valve replacement (TAVR) or transcatheter aortic valve implantation (TAVI) interventions. In these or similar procedures, one or more tools/devices may be resident at least at times in the FOV of imager IA. Some of the tools/devices may be movable and/or may be capable of assuming different shapes/states.

Operation of the imaging apparatus, in particular image acquisition, is controlled by the user from an operator console or control unit OC. Operator console may be arranged as a dedicated computing unit communicatively coupled to the imaging apparatus. The operator console may be situated in the same room as the imager IA or in an adjacent "control room". Remotely controlled imaging systems IA connected through a suitable communication network to a control unit OC, located possibly remotely from the imaging apparatus, is envisaged herein in embodiments. Autonomous imaging system are also envisaged herein, where the control unit OC operates fully or semi-autonomously, without or with little user input.

The imaging control unit OC controls the imaging operation by setting certain imaging parameters IP. The imaging parameters determine or at least influence the contrast mechanism and hence the image quality of the produced imagery to be processed by the system SYS. The intensity values (and hence the pixel values) as captured in the recorded imagery can be influenced by changing the parameters and this is frequently done because different phases of the medical procedure may call for different imaging settings as usually described by medical imaging protocols. In X-ray imaging, the imaging parameters include for instance settings of the imaging geometry. The imaging geometry describes the spatial relationship between the imaged patient or at least a region of interest ("ROI"), and the X-ray source and/or a plane of the detector D. The imaging geometry thus determines in particular the projection direction d. The imaging geometry determines the current FOV. The imaging geometry and thus the FOV may change dynamically during the intervention as requestable by the user setting different imaging parameters. Other imaging parameters of the imaging geometry may include a collimation parameter. A collimation parameter pertains to a collimator (not shown) of the imaging apparatus IA. The collimator may comprise a number of X-ray opaque blades which can be adjusted through the operator console OC by setting the collimation parameters to so define an aperture of a desired shape and/or size. Controlling shape/size of the aperture allows restricting or widening the X-ray beam thus further defining the FOV.

The imaging parameters may also influence the very nature of the X-ray beam and hence the manner in which the x-radiation interacts with patient tissue thus influencing contrast in the captured imagery. The nature of the x-radiation may be determined in particular by settings of the X-ray source XS. In embodiments, the X-ray source XS is an X-ray tube ("tube" for short) including a cathode and an anode. One such imaging parameter may pertain to the amperage and/or voltage of the X-ray tube. Imaging parameters for the tube operation are collectively referred to herein as (X-ray) source parameters. The X-ray source parameters may prescribe in particular the energy of the X-ray beam. Source parameters may depend on the specific imaging protocol or modality. In embodiments, the main application envisaged herein is fluoroscopic X-ray imaging. A C-arm or U-arm imaging system IA as sketched in FIG. 1 may be used for fluoroscopy. In fluoroscopy, the envisaged beam energy is usually in the range of 50-60 keV. Other applications may call for other energy ranges.

The imagery acquired by the imaging apparatus includes image structures or feature(s). Image structure/image feature is the variation of patterns of the pixel values in the captured imagery which may vary spatially across the image plane. Types of image structures may include geometrical structures or appearances at one or more scales, geometrical configuration (position, rotation, shear), gradients, color or grey value distribution, etc. In particular with X-ray imagery, such structures are a function of projection direction for a given object in 3D. As will be explained in more detail, such image structures may be local or global. Image structures may be manifest in spatial domain but may be manifest in addition or instead in frequency domain. Image structures may be quantified or detected by thresholding or other analysis in spatial or frequency domain. Fourier or Laplace transform-based techniques, or Wavelet techniques or any other such techniques, may be used. Whilst in the following the description will mainly focus on image structures in spatial domain, this is not to limit the present disclosure in any way and the ML principles described herein are readily applicable in the frequency domain also, and such applications in frequency domain are specifically envisaged herein in embodiments.

Ideally, the image structures captured in the imagery corresponds to the task at hand to provide the necessary information such as for navigation purposes or diagnosis. For example, patient characteristics (gender, BMI), different organs, tissue type and/or their mutual spatial arrangement may cause different image structures to be recorded in the acquired imagery. The system SYS analyzes the image structures as encoded in the imagery to compute the result RS.

There are many contexts in which different types of image structures may arise. One such context has been described above by way of the imaging parameter. This context may be referred to herein as the imaging context. Other contexts include a patient context. Specifically, as mentioned, tissue type and their spatial arrangements etc, in a given patient give rise to certain types of imaging structures. The image structures may represent normal, expected anatomies but may also be caused by the patient presenting with unexpected physiological or anatomical features, such as bone fractures, tumors, etc.

Yet another context in which image structure arises includes a procedure context. The (medical) procedure context relates to medical tools, devices and equipment used during the intervention, or at least during parts of the intervention, whilst the imagery is acquired. Such tools, device and equipment may reside at least partly and at times in the FOV. Such medical devices may be introduced from the outside into the patient during the intervention such as the mentioned balloon catheter, guide wire, guiding catheter, microcatheter, introducer sheath, pressure guidewires, robotically steered guidewires and instruments, sensing catheters, imaging systems such as transesophageal echocardiography (TEE) probe or intravascular ultrasound (IVUS) or an optical coherence tomography device, any catheter with sensing capabilities e.g. spectral sensing, a laser atherectomy device, a mechanical atherectomy device, a blood pressure device and/or flow sensor device, a shape-sensed device (Philips "FORS"), needles, ablation electrodes, cardiac electrophysiology mapping electrodes, balloons, endographs, stents, stent retrievers, aneurysm coils, and a plethora of other therapeutic or diagnostic tools such as mitral-valve clips, pacemakers, implants, other artificial heart valves, blood vessels, etc. Other medical tools or devices may already be resident in the patient such as from previous interventions, for example implants etc. Because such medical tools or devices may be resident in the field of view, they too influence the image structures that are recorded and encoded in the acquired imagery. For example, medical tools such as a guidewire are made of high opaque material such as steel and may thus induce distinctive projection shadow(s) ("footprint(s)") in the medical imagery in form of a snake line for example. This is illustrated as an example in FIG. 4A where a projection footprint $\pi(r2)$ of a portion of a guidewire r2 is shown. It will be understood that the three contexts described above (procedure, imaging and patient context) may overlap.

Referring now to FIG. 3A,B, and in more detail to the machine learning system SYS, this includes in embodiments the pre-trained ML model M that has been adapted based on training data, such as historic patient imagery sourced from medical data repositories. The training data is held in on one or more training data memories MEM-TD. A training system TS, implemented on one or more computer systems, processes some or all of this training data as held in the training data base(s) MEM-TD. The training system TS adjusts parameters of r the model M to so train the machine learning model M. Non-model based approaches are also envisaged herein, where input during deployment is adapted based on training data itself, to arrive at the result RS.

The performance of the computerized ML system SYS may depend on how well the machine learning MLM has been trained. The quality of training will depend at least in part, on certain features of the training data set TD used. The training data set comprises usually a large number, possibly in the order of hundreds or thousands, specimens of training imagery. The imagery may be associated with additional data. The additional data may be textual such as health record extracts or header data included in the imagery or any types of annotations (segmentation, object location, contours, diagnostic findings, etc.). The header data may describe the imaging or procedure context as discussed above. To facilitate good training outcome, the training imagery is preferably drawn from a patient population representative of the task for which the model is to be trained for. However, even if the training data is representative for the patient population and the task of interest, this may still not suffice to ensure a good quality training and hence good performance of the machine learning model. This is at least in parts because of the influence of the above mentioned various contexts on the image structures captured in the training data set.

More specifically, not all of the training data, even for a given patient, is affected in a uniform manner by one or more or all of the above mentioned contexts. This can be most easily seen for medical interventions, where a medical devices BC such as, for example, a balloon catheter is used. The imagery is acquired by imager IA during the intervention, but the balloon catheter BC may not always be present in the field of view because it is simply not always required during the whole of the intervention. Different tools may be used during the intervention. Such tools, implements, devices, etc, may be exchanged, removed and/or placed back into the field of view, etc. This dynamics of a context induces, for machine learning purposes, undesirable bias in relation to image structures that may lead to poor performance of the machine learned model.

As mentioned, in over-fitting the machine learning model M memorizes the recorded image structures rather than learning the general underlying principle for the task of interest. But another undesirable effect of main interest herein is caused by the bias in a given data set. A large number of machine learning algorithms or models M is configured to find latent correlations between the training imagery and the results of interest, also referred to as targets in training phase. If some specimens of the training data do include image structures such as projection footprints of medical tools for example and some do not, then this difference may constitute an undesirable statistical bias in the data. This bias may prevent the machine learning model/algorithm to learn relevant features and correlations specific to a given task. Thus, if the (original) training data includes a consistent feature/structure that is completely unrelated to a task one wishes to train the ML model for, than this is referred to herein as bias.

For example, in order to train the model M for image-based diagnosis for a certain medical condition, the presence, for example, of a projection footprint of a catheter in one part of the image may be entirely irrelevant for this task. And yet, the machine learning model or algorithm may still erroneously account for such a presence and thus yield sub-optimal training results of the actual diagnostic task of interest.

It is proposed herein a system TDM that is configured to eliminate, or at least reduce, such bias or spurious correlation building effects caused by image structures irrelevant for the task of interest. The system TDM proposed herein processes the training data prior to learning to improve the training data set. The proposed system TDM is thus configured for data preparation, sometimes also called data augmentation, or data-driven regularization.

With continued reference to the block diagram FIG. 3B, this shows schematically the data preparation system TDM as envisaged herein in more detail. The system TDM may include a training data modifier DM. The system TDM may be implemented by one or more computer systems PU. The training data modifier DM processes the training data to be used by training system TS for train the machine learning model M. Alternatively, the training data processed by data modifier DM may be used in non-model based schemes to compute the result RS.

The data preparation system TDM is operable to reduce the effect of bias by modifying the existing training data set. To do this, the training data system TDM analyzes the training imagery, in particular X-ray training imagery, and reduces or removes, or adds certain image structures in some of the imagery from the original set TD. In other words, the training data system TDM performs a modification operation on (some) of the original data, to so cause the (new) training data set as a whole to represent a sample having a wider statistical variance with respect to certain structures caused by one or more of the above mentioned contexts. Thus, by operation of the proposed system TDM, variability in the original training data set is increased. For instance, distribution of the initial training specimens might be very narrow (with low variance), or may be shifted by an unknown bias. By adding new modified specimens, the system TDM in effect widens the distribution curve (increases the variance) or shifts the distribution to remove or reduce the bias. Some or all of the original specimens are preferably maintained and not replaced by the modified imagery, thus in effect enlarging the training data set. The enlarged set of training data has thus a higher variability in terms of image structures/features.

For example, in X-ray imagery captured during interventions, the projection footprint of the balloon catheter may not always be present for each image. This may lead to the machine learning model constructing spurious correlations which is undesirable. To improve the statistical quality of the training data set, the modifier MD may add a synthetically generated, but preferably realistically looking, projection footprint of a balloon catheter to those images in the training data set where no such footprint is shown natively. This modification by adding suitable image structures produces modified training imagery which is then added to the remaining specimens of imagery in the data set that already had the footprint encoded therein natively. Operation of the training data modifier system TDM thus results in a prepared or "augmented" data set, including the modified image specimens and some of the original image specimens that did not need modification. Preferably, the original specimens that were modified are also maintained in embodiments, thus causing the higher variability in the set.

Modifying the existing training data set by adding image structures is merely according to one embodiment. Alternative embodiments are also envisaged herein that do the opposite. In such embodiments, image structures are removed rather than added in order to make the information content in the training imagery more variable/varied for machine learning boosting purposes. For example, instead of adding a projection footprint of the medical device that was not there before, it may be an alternative option to instead identify the imagery where such footprints are encoded natively, and then to remove same. However, adding image structure appears more favorable as removal of structures may introduce inaccuracies which may in themselves may mislead the machine learning algorithm to build other spurious correlations. Whether or not modification is by removal or addition may be switchable and may be conditioned on certain events. For example, the training imagery may be analyzed first, to ascertain which set is larger, the one comprised of imagery having the respective footprint or the set comprising the imagery that does not. The smaller set may then be processed instead of the larger one, by adding or removing image structures as the case may be. This set-size-analysis may thus save CPU/GPU/TPU time when performing the modification operation.

Modifying the training data set in the manner described allows constructing a new training data set, preferably including the original, unmodified imagery, and the newly added artificially modified ones. It is thought that the new data set may thus better approximate a test data distribution that is unknown at the training phase, thus resulting in the machine learned model trained on this new data set being able to better generalize to data it has not seen before. By adding/using the new artificially modified image specimens to/with the original training data set, larger variability is achieved and a possible bias in the original set can be compensated for.

The trained system TS operating on the so prepared training data, including the modified image specimens, will in general perform better, will be less prone to undesirable bias effects and the construction of false correlations. The proposed system is configured to cope with unique features found in X-ray projection imagery such as superposing projections of separate 3D objects in the projection plane and merging of foreground and background features. The cope with such effects, the proposed system includes projection techniques to cause the modifications. Preferably, the modification operation is constrained by prior anatomical knowledge as will be described in more detail below.

The modification of the training data set by modifier system TDM may be done fully automatically or may be done based at least in parts on user input, receivable through a user interface UI, such as a graphical user interface. The user can thus add image structures thus leveraging their medical knowledge. This and other embodiments will be described in more detail below.

As described, not all of the training imagery of the training data set as held in the storage MEM-TD may need to be modified. For example, if the projection footprint of the medical tool, such as of the balloon catheter, may need to be added only those images that do not natively encode this. A similar qualification applies for an image structure removal operation. The training data modifying system TMD may thus include a filter or selector SL. The user can specify one or more of the above mentioned contexts he or she wishes to be accounted for in the training data preparation. The selector SL then scans the available imagery first, and selects those images that could benefit from modification. In one example, the selector may include a segmentor module that segments the imagery for projection footprints of interest, such as those of the balloon catheter, which is known a priori. Those images that do not include the footprint can then be marked up and prepared for processing by the training data modification system to have a synthetically generated projection footprint of a balloon catheter model added thereto. Alternatively, and as described, the filter SL may be used to find those specimens that do have the footprint natively encoded so as to have same removed by the training data modifier system TDM. The balloon catheter is merely one example, and other device footprints may be processed accordingly. The selector SL however is optional, as the in some cases the modified imagery may be allowed to include multiple such footprints of different or the same device, the native ones and the synthetically added ones.

As mentioned, in embodiments, the training system TS uses an ML algorithm to adjust an initial set of parameters of the ML model M, based on the training data. The training data modifier system TDM may be implemented on the same computing system as the training system TS, or may be implemented on separate systems. Training system and/or the training data modifier may be implemented on a single computing system or on plural such computing systems, such as in a distributed architecture as is envisaged herein in embodiments. Each of the training system TS and the training data modifier TDM may be implemented in hardware, in software or partly in both.

The training data preparation or modification as implemented by the training data modifier TDM may be done up front, in a preparatory phase prior to operation of the training system TS, for all or some of the training images to produce the improved or augmented training data set. It is thus the so prepared or augmented training data set that is then processed by the training system TS in the later training phase to train the model M. However, operation of the training data modifier TDM in such a preparatory phase prior to operation of the training system TS may not always be required and a joint operation of the two systems TDM, TS are also envisaged in embodiment. The two systems may hence operate in an inter-leaved mode where process flow oscillates between the two systems TMD, TS. For example, the training data modifier TDM may operate on a certain sub-set of training data to modify same. The modified data is then added to the training data set. The training system TS then accesses some of the training data set in batches for example, in sub-sets, which may or may not include some of the modified training data set. In fact, it is mainly envisaged herein that a random operation is used by training system TS to select a batch from the training data set which may or may not include a certain proportion of modified training data. Training by training system TS then proceeds on the selected batch. In the next iteration cycle, process flow then returns to the training data modifier TDM, which then again modifies a next subset of training data, and adds these to the training data set from which then a new batch is drawn and processed by the training system, and so forth. An embodiment of this interleaved operation of training data modifier TDM and training system TS will be described more fully below at FIG. 7. However, as such, the training data modifier system TDM is a standalone system and not necessarily tied to any training system TS.

In addition or instead of the randomized selections of the batches by the training system TS, the training data modifier TDM may also be randomized in selecting by a random operator which ones of the original training data to modify in the first place. Preferably, but necessarily, operation of this randomized selection for modification may be restricted to the set previously earmarked by the selector SL, comprising imagery that can benefit at all from such modification.

Figure 4:
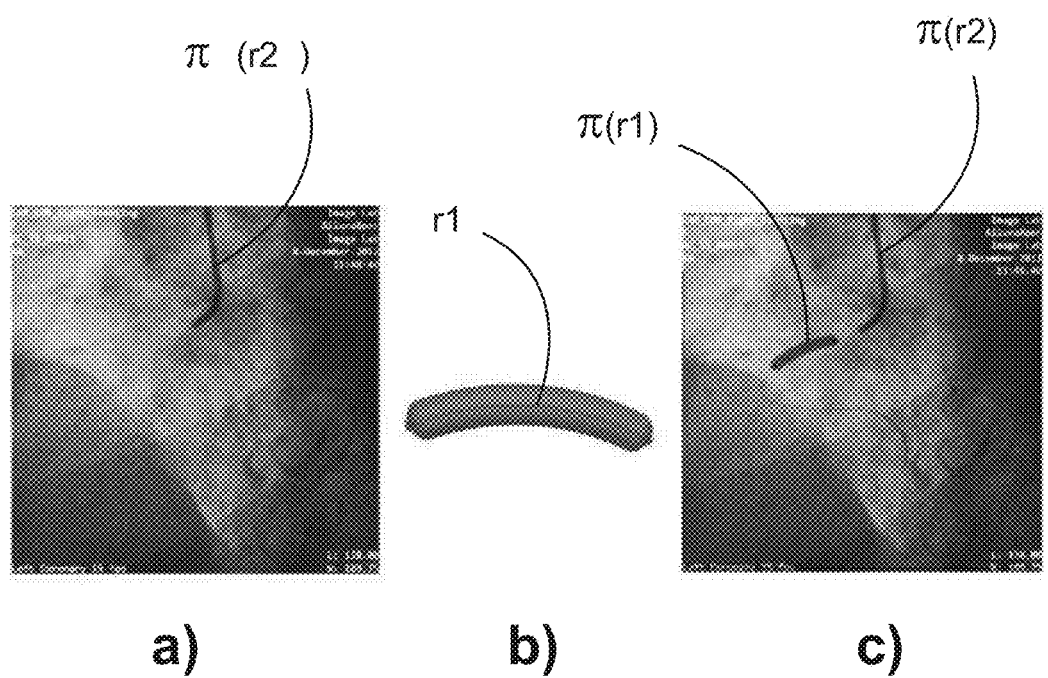
FIG. 4 shows a modification operation that includes superimposing on an X-ray image a projection footprint of a model of a medical device.

Continued reference is now made to FIG. 4, where a modifying operation of the training data modifier DM is illustrated for fluoroscopic imagery in relation to a balloon catheter. As mentioned earlier, FIG. 4a) shows an X-ray image frame as acquired which natively includes a projection footprint $\pi(r2)$ of a guide wire r2. The balloon catheter is usually slid over the guide wire. Such imagery may cause undesirable correlations to be constructed in training if most of the other frames do represent different phases of the medical procedure in which the balloon catheter is not present in the field of view. Now, in order to compensate for the procedure context and to remove this bias, a computerized CAD model, such as a mesh model of a deflated or inflated balloon catheter, may be accessed in a memory by the training data modifier DM. One such three dimensional model r1 is shown schematically in FIG. 4b). FIG. 4c) shows the result of a modified image obtained by adding the projection footprint $\pi(r1)$ of the model r1 to the native image as per FIG. 4a). The balloon catheter footprint, or the projection footprint $\pi(r1)$ or other such a device, is added in proximity to the guide wire footprint $\pi(r2)$, because this is a natural realistic position as the balloon catheter is usually slid over the guide wire as mentioned above. It is thus envisaged herein to constrain the preferably randomized modification by modifier DM of the training imagery to take into account medical and/or anatomical knowledge or any other contextual knowledge to so ensure that the synthesized, artificially created modified imagery remains realistic or consistent. This allows avoiding producing unrealistic imagery that may be detrimental to the performance of the machine learning module as this too will cause unwanted bias.

Figure 5:
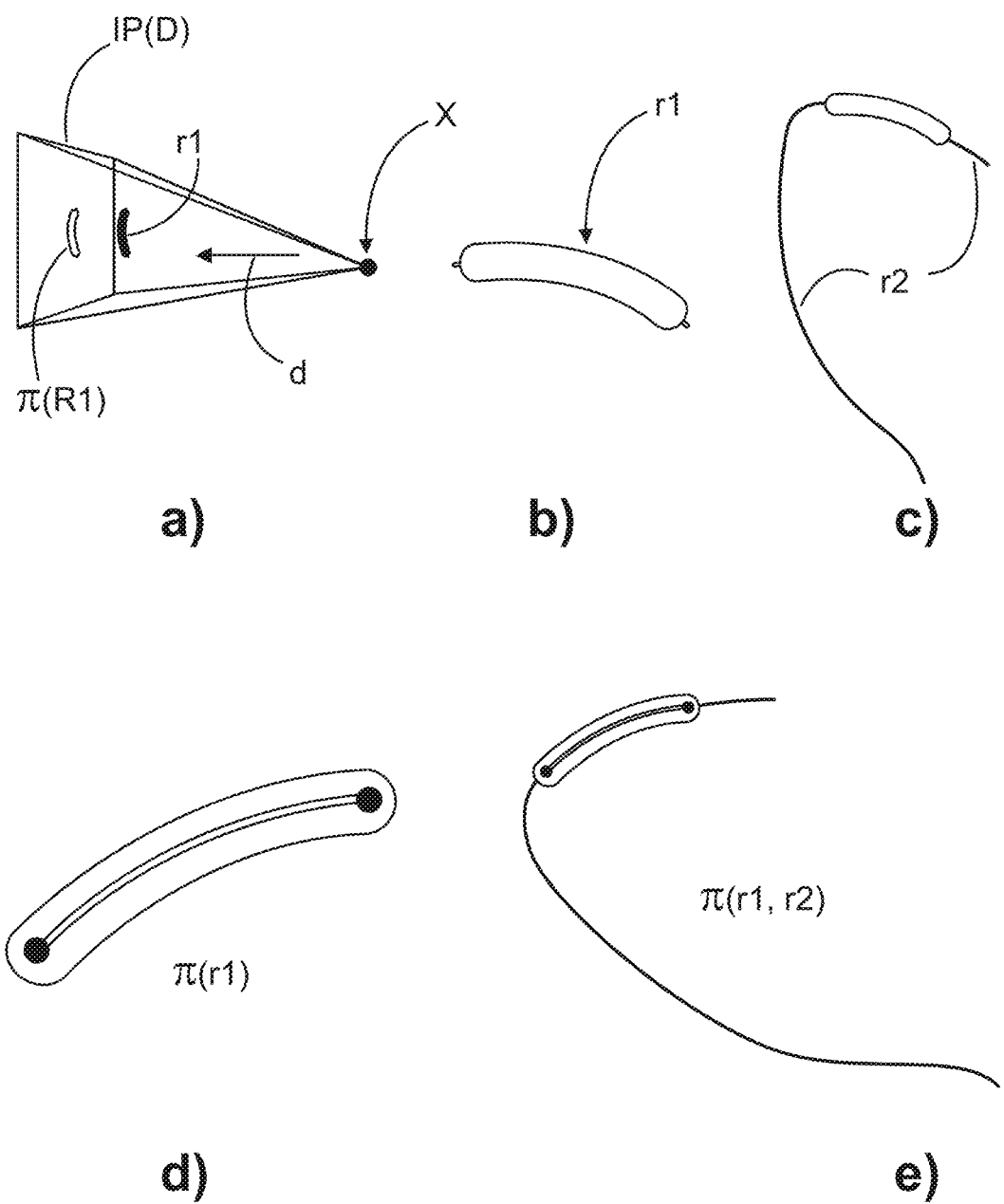
FIG. 5 shows further details of the modification operation including projection footprints of models of medical devices.

FIG. 5 further illustrates the modification operation of adding projection footprints of medical tools such as of a balloon catheter r1 and/or guide wire r2. A classical geometry based ray tracing algorithm may be used as shown in FIG. 5a). The desired orientation and position of image plane IP(D) of the conceptual detector D is specified and so is the location 'X' of the conceptual X-ray source XS. From the source position X, rays are cast which intersect the image plane IP(D) along the desired projection direction d. The model r1 of the to be projected device is then positioned and oriented in between plane IP(D) and source location X to be intersected by said rays to so find the projection footprint $7r(r1)$. The synthetically generated projection footprint $7r(r1)$ may then be added to the image 4a) that natively does not show this footprint. FIG. 5b) shows a geometrical mesh model of the balloon catheter r1 and FIG. 5c) shows a combined model of balloon catheter r1 and the guide wire r2. FIG. 5d) shows a close up of the projection footprint of balloon catheter model r1. FIG. 5e) shows the combined footprint $7r(r1,r2)$ of the balloon catheter and the guide wire.

Figure 6:
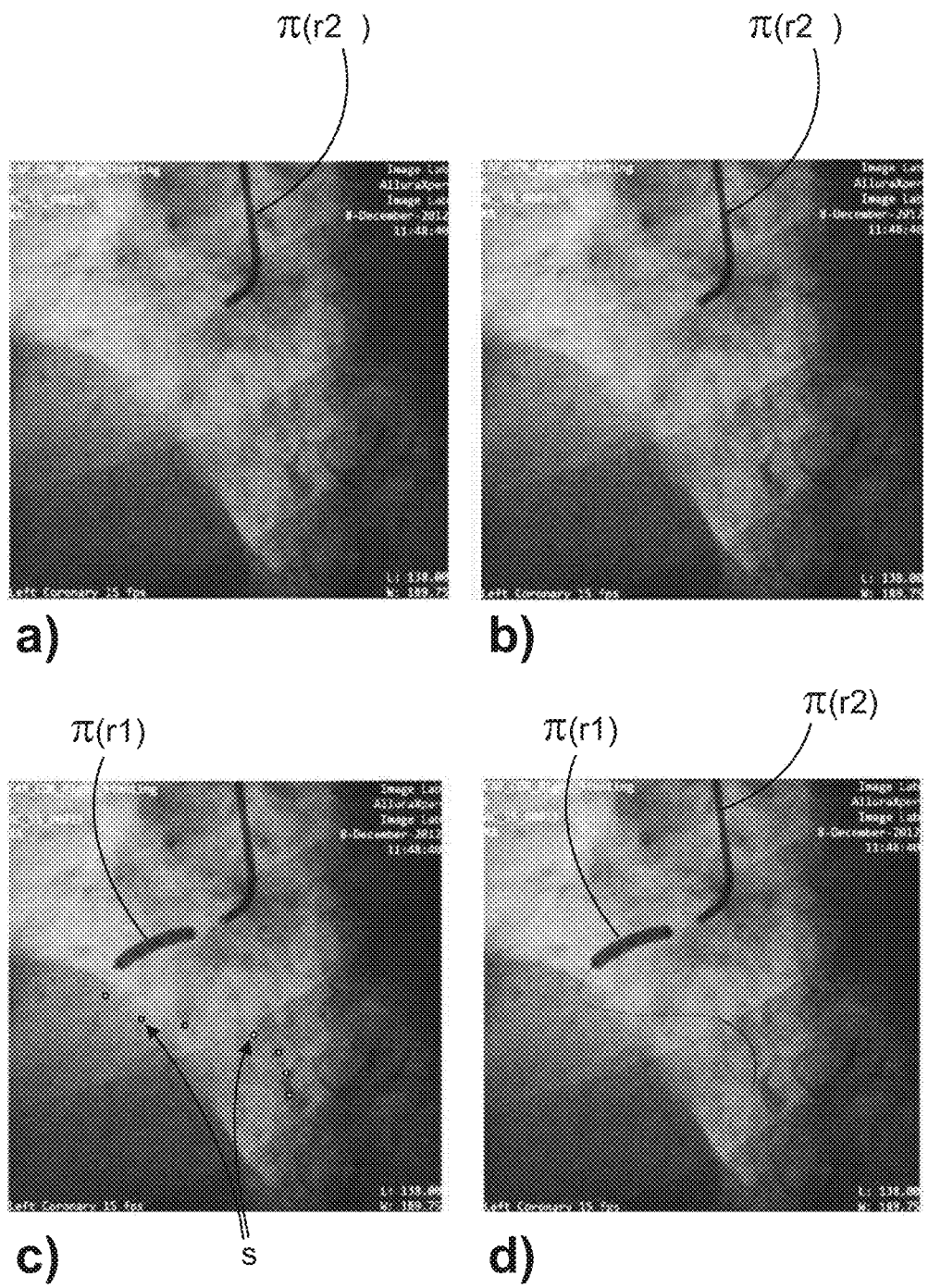
FIG. 6 shows a user interaction based modification operation to include an additional image structure into an X-ray image.

FIG. 6 further illustrates operation of the training data modifier TDM with user interaction. For example, in order to modify with user input the input image to include synthesized projection footprints of one or more medical devices, such as the balloon catheter and guidewire, the training data modifier TDM may proceed as follows. First, a projection footprint of the balloon portion is blended with the original image u as shown in FIG. 6a). This modification may be displayed to the user, FIG. 6b). Next, and as shown in FIG. 6c), the user may use a user interface UI, such as a pointer tool, a computer mouse or a stylus or other, to define and place a set of one or more control points S in the projection imagery to be modified. The training data modifier TDM may use a spline algorithm to pass a snake line through the user designated control points S, to so generate a realistic looking synthetic projection footprint of a guide wire that meets the previously or later placed projection footprint π(r1) of the balloon catheter. The positions and orientations of plural models r1, r2 can thus be generated consistently. The spline curve is overlaid on the original X-ray image u to obtain the modified image u' as final output as shown in FIG. 6*d*).

Figure 7:
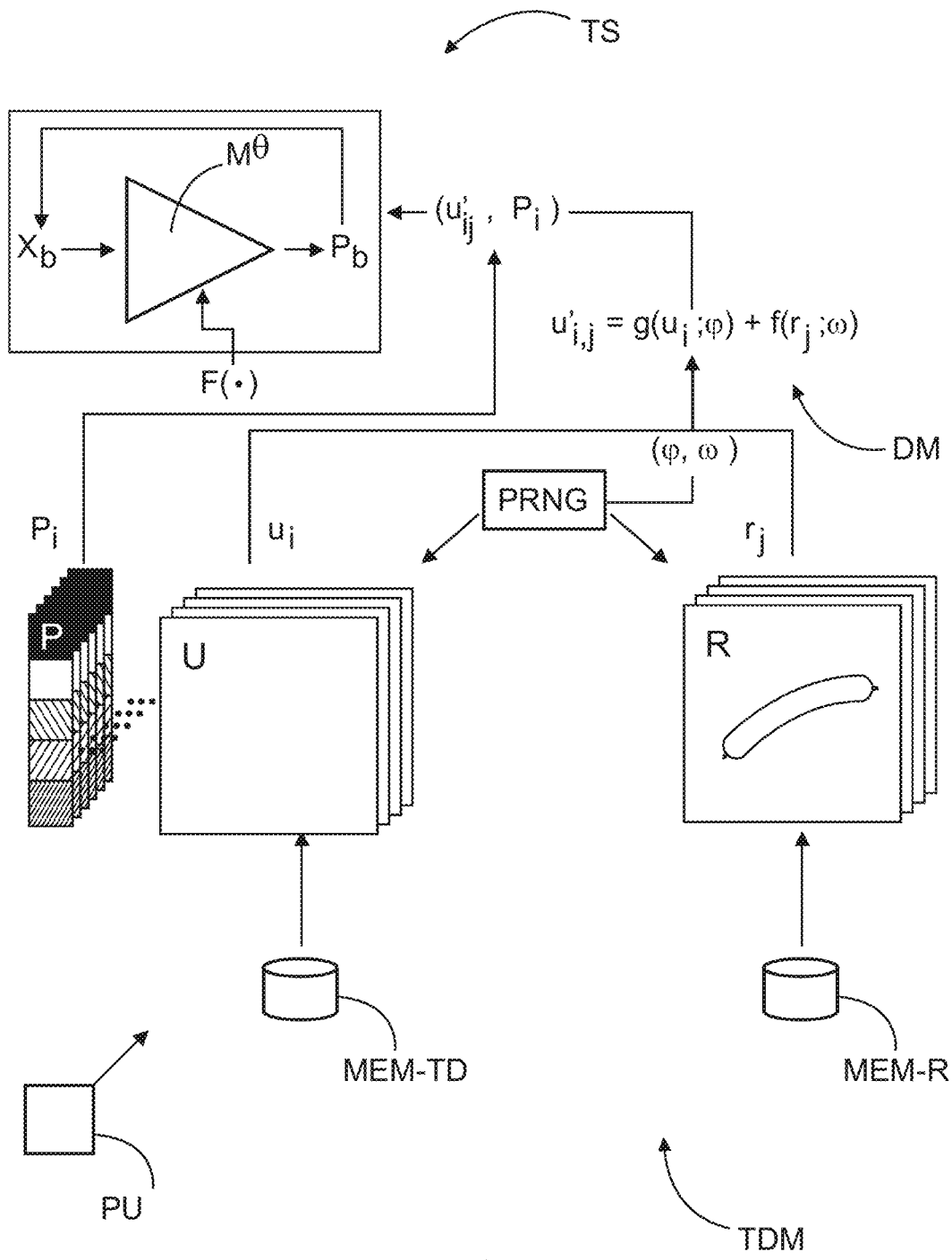
FIG. 7 shows a block diagram of a training data modifying system as envisaged in embodiments in co-operation with a machine learning training system.

Reference is now made to the block diagram of FIG. 7 which shows operation of the training data modifier TDM in conjunction with the training system TS in interleaved mode as briefly mentioned above.

The training data modifying system TDM includes the data modifier module DM as shown in FIG. 7. Operation of the modifier module DM is preferably randomized by operation of a random selector PRMG implemented as a pseudo-random number generator.

The training data modifier TDM and the training system TS may be implemented on a single processing computing unit PU or may be implemented on a plurality of processing computing units PU, preferably connected by a suitable communication network to exchange data.

Operation of the of the training data modifier system TDM system is now explained in more detail.

The system TDM has access to an original (as yet unmodified) training data set U, including X-ray imagery from historical interventions on previous patients. The set U is stored in a storage MEM-TD, a database or other memory. The data Uis preferably labeled ground truth data. For example, the data set U consists of a training imagery u, some or each labelled with information P in any one or more of the following formats:

Stent type A (0), Stent type B (1) labels for binary classification;

Binary mask of the tool or device for segmentation tasks, where device or tool is represented by 1 and background by 0;

Bounding box around the device or tool for detection/tracking task; or

Position of the device or tool in respect to some reference (anatomical) coordinate system for pose regression or other regression task.

However, the above a.-d. are merely examples of envisaged labelling, and other labeling schemes are also envisaged. The type of labelling is a function of the task one wishes to train the ML model M for. The labelling may be done by a human expert or by using scripting tools to search databases for the relevant information and prepare suitable associations between image u and label P.

The training system TS includes storage to store an ML model M. The model may be a neural network type model, including computational nodes arranged in layers. There may be an input layer and an output layer, and one or more hidden layers, the network having thus a deep architecture. The network may be a deep convolutional neural network. The training system trains the model M on an application specific task involving X-ray data, such 2D fluoroscopic images from percutaneous coronary procedures. For instance, the neural network could be trained to predict type of the device as represented by the image, or regress a bounding box around the device. The number of intermediate/hidden layers depends on the complexity of the task. The task for which the network is trained may be specified in particular by the last layer, the output layer. Some or all the intermediate/hidden layers may be convolutional layers, each comprising a convolution operator, and any one or more of: a non-linear operator (activation function), batch normalization operator, dropout operator, spatial pooling operator, or other operator. Tasks that the network can be trained for may be a classification task. The classification task may be multi-class or binary, e.g. "device type A vs device type B". The classification task may include segmentation tasks, such as a segmentation for the guidewire or other device used during the intervention. The tasks may be one of detection/tracking, e.g. detection of a mitral valve replacement device, such as MitraClip. A regression task may include, e.g. pose regression, i.e. position and orientation of the device with respect to some reference anatomy. Generative tasks are also envisaged, such as text generation, e.g. creation of reports based on the input image, etc. Any other suitable from-image-inferring task for medical purposes is also envisaged herein. The training system TS may be configured for (mini-)batchwise training.

Operation of the data modifier DM is now explained in more detail. Based on an index provided by pseudorandom number generator PRNG, the modifier TM randomly choose a 2-tuple (u,P) from the ground-truth datasets (UP), where P is a label for a training case u. For example, u is an X-ray image of an interventional device, and P is a binary mask on which the device projection footprint is represented by "1", and background by "0".

The modifier DM may then combine training case u from the selected 2-tuple with a projection of a device model, e.g. projection footprint catheter, such a (drug-coated) balloon model r. The model may also be randomly chosen from a set of models R using the PRNG. Training case u and device model r can be preferably combined using one or combination of the following methods that are known in the art. For example, weight-based image blending may be used:

$$u' = \varphi u + \omega r, \text{ where } \Omega = 1 - \varphi \tag{1}$$

instead of or in addition to spatial domain-based blending, frequency domain based modification such as Laplacian pyramid blending may be used. Other options envisaged herein include any one or more of selective, region-based blending, two-band blending, graph-cuts based blending, or others segmentation based blending techniques. The data modifier TD may calculate the projection footprint of the device model. Projection of the device model is simulated from a 3D mesh model of the device for example, using X-ray simulation algorithms known in the art, such as probabilistic Monte Carlo methods, or deterministic or analytic variants thereof, in combination with geometrical ray-tracking algorithms.

Depending on the type of context one wishes to augment for, the input X-ray image may be modified to include, in procedure context, projection footprints of devices such as heart replacement devices, such as mitral valve clip. Other medical devices whose projection footprint may be used include any one or more of a trans-esophageal echocardiography probe, the mentioned guidewire or catheters, FORS guidewires, clips, pacemakers, electrode, needles for biopsy and/or therapy as well as foreign objects. Patient-internal devices are also envisaged, such as orthopedic implants, such as bone screws, plates, wires, etc.

In the patient context, the modification operation may include introduction in the image u of structures representative of anatomical abnormalities, such as bone fractures, deformations, etc.

In the imaging context, the modification operation may include introduction in the image u of structures representative of alteration of the imaging parameters, such as collimation parameters (eg, more conservative collimation setting), alteration of gain, filters, magnification, and other imaging parameters still.

The set R of r device projection models are a priori created using methods known in the literature, such as probabilistic Monte Carlo method, or deterministic or analytic variations thereof, based on X-ray-tracking algorithm, as earlier shown above in FIG. 5. The device models may be held in storage media in the following format: R={$r_1$, $r_2$, ..., $r_m$}, each $r_j$ representing a different model.

An initial training dataset U consisting of X-ray training cases u is collected and automatically or manually labelled by the expert users, with vectors p and may be finally stored on the storage MEMTD as a 2-tuples (u, p):

$$(U,P)=\{(u_1,p_1)_1,(u_2,p_2)_2,\ldots,(u_n,p_n)_n\} \quad (2)$$

The modified training images (u', p') with their original or updated label are accessed by training system TS. The training system TS may run a batch-wise training scheme of a convolutional neural network (CNN) model. Non-batch-wise training are also envisaged, and so are ML models other than CNN. The training procedure implemented by training system TS may run through plural iterations. At some or each iteration, a generated batch ($X_b$, $P_b$), which comprises $1 \le b \le m$ randomly selected labelled training images (presented as 2-tuples), is fed into the model M. The model M has a preassigned structure and an initial set of network parameters, sometimes referred to as weights in an NN-type model M. The network accepts the batch $X_b$ at its input layer and transfers the ground truth set $P_b$ to its output layer, directly or indirectly. At some or each iteration of the training process, these weights are updated by propagating errors between the model-predicted output and the ground truth, first in a backward direction and then in a forward direction. The weights are iteratively adjusted, until the error drops below a threshold. Stopping criteria other than threshold based, for instance early stopping regularization technique may also be used instead. The selection of the batch is preferably randomized by using PRNG as mentioned. Consequently, in the notion above ($X_b$, $P_b$) for the batch, "X" refers to either a modified image u' or an original image not processed by the training modifier TDM.

Figure 8:
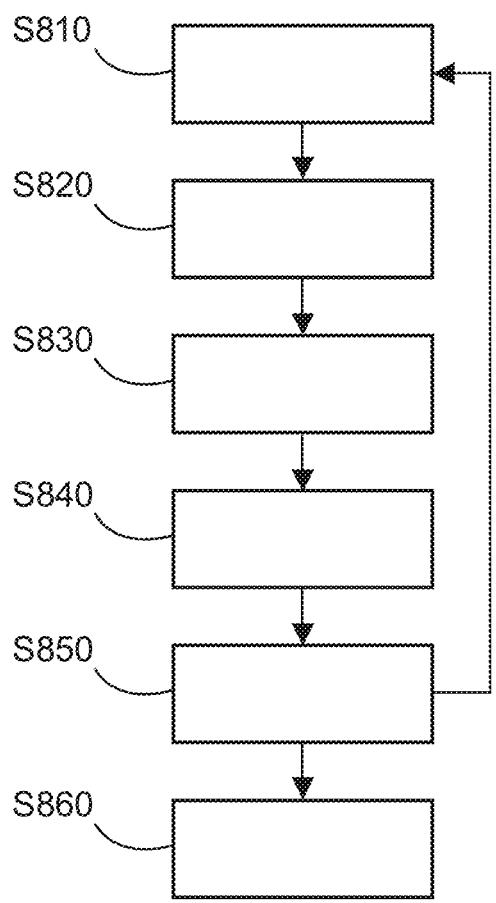
FIG. 8 shows a flow chart of a method of modifying training data for use in machine learning.

Reference is now made to FIG. 8 which shows a flow chart of a computer implemented method for modifying a training data set for machine learning. The proposed steps to be described below can be used to implement the training data modifying system TDM as described above, although it will be understood that steps described can also be understood as a teaching in their own right, not necessarily tied to the architecture described above in relation to FIGS. 1,3 and 7.

Also, whilst the system and method will be described with main reference to X-ray imaging, in particular fluoroscopy, the projection of synthesized projection footprints into imagery is but one way of modifying training imagery. It will be readily understood by those schooled in the art, that the described system and method can be used also for other medical interventions or medical procedures, and may then comprise other ways of combining or modifying the imagery, other than by projecting a synthesized footprint of one or more models of such medical tools, implements or devices, as may be used in the intervention or procedure. Specifically, much of the above described modification operation are configured to compensate for procedure context. This was done partly to illustrate the concept. In order to prepare the training data in respect of one or more of the other contexts, such as patient context or imaging context, other types of modifying operation may be called in order to suitably compensate for the respective image structures.

Further still, the above described modification operation by adding or removing synthesized projection footprints of geometrical models $R_j$, cause merely local changes in the modified training imagery. However, global changes may be called for when modifying in respect of other contexts, such as the imaging context, where the whole of the respective training image may be modified. Some of such global modifying operations may be understood as simulations, and will be explored more fully below.

Referring first to step S810, an X-ray image u to be modified is selected from an initial training data set U. As previously describe, this step may include a filter or pre-selection step, where the initial training data set is subdivided into classes including those that are to be modified and those are not modified, respectively. As to which images are to be modified will depend on the context (including the above described, such as medical, patient or imaging) one wishes to account for in the modification operation. In embodiments, the selection of which image(s) u is/are to be modified is randomized. More particularly, in one embodiment, a random X-ray image is selected from the training data set U, or is selected from the subset of preselected images. A random number generator may be used for this randomization.

Preferably but not necessarily the training data set U has been labeled as is frequently done for supervised learning schemes. Thus, some or each image in the training data set U is associated with a corresponding label P. The label P represents the training target and relates to the task or result one wishes to train the model for, such as a classification task for instance. For example, the label P may indicate the presence of a certain disease or medical condition. The label is thus a classification label P that indicates a type of medical condition. The label may be binary ("0" or "1") to merely indicate whether or not the specimen is indicative of a certain disease/medical condition. However the data modifying method and system described herein can be used for unsupervised learning also, in which case no such labelling is required.

At an optional step S820, and with main reference to the example of modification by projection, a device model r to be used for computing the projection footprint is selected from a data set R of device models. The device models r may relate for instance of a balloon catheter, a guide wire, other types of catheters, or any other medical tools such as the mitral valve or clip, or any other medical device that may reside in the FOV. The model r may be a CAD model, such as a polygon mesh comprising edges and vertices, resident as a suitable data structure in a model memory.

At step S830 the selected image at step S810 is modified so as to improve the training data set U as a whole to establish a modified or "augmented" training data set U'. The so improved training data set U' may facilitate avoiding over-fitting or the establishing of false correlations when, at a later stage, a machine learning algorithm uses the improved training data set U'. Such use may include training an ML model M, or computing a result based on the set directly, as in non-model-based ML. The modification may be done on-the-fly/on-demand as described above at FIG. 7, so that at no stage are all image specimens of the new set U' held as a whole in memory.

In one embodiment, the modification at step S830 is done by combining projection footprint for the device model as selected at step S820 with the X-ray image selected at step S810. More particularly, this embodiment may include projecting the model r along a pre-defined projection direction d by using a geometrical algorithm, such as X-ray casting.

A shadow or projection footprint π(r) of the model r is computed. The computation is based on fixing the model r in a selectable position relative to the image plane of the X-ray image u, and a selectable position X of the virtual X-ray source. Virtual rays along direction d are cast to effect the projection. The direction d, position X and the orientation of image plane IP(D) may be user selected or may be automatically retrieved from imaging parameters/imaging protocols that were used to acquire the image u. The imaging parameters are sometimes found in image header data, such as when the image u is of the DICOM format. The imaging parameters may be associated otherwise with the image u and may be found instead in other databases or in patient health records, etc.

Once the extent, position and orientation of the projection footprint is defined in the plane of image u, the projection footprint π(r) can then be combined with pixel values at the respective locations as recorded in original image u. In particular, pixel values for the projection footprint π(r) having a known radiation opacity can be merged with the pixel values as natively recorded in the X-ray image u at the area where the computed footprint is to be blended in. The footprint is thus superimposed on the image as an overlay structure. In embodiments, arbitrary transition functions f and g may be used which may be weighted with weighting parameters φ and ω as described above at eq (1).

The transition functions and weights describe the relative opacity/visibility of the footprint pixel values and native pixels values. In general, the known pixel values of the projection footprint π(r) are combined by linear combination with the natively recorded pixel values at in the respective area/location. The weights φ, ω are either fixed/deterministic or randomly chosen. The position of the projection footprint π(r) depends on the relative position of the model between image plane and source position X. In simpler embodiments, the position of the projection footprint π(r) may be held constant for some or all of the images modified, and the same footprint may be reused. However, for more realistic results the position of the synthesize footprint may vary for some or all of the modified images. The positon may be varied deterministically, by placement at different corners of the image for example. Alternatively, the placement of the projection footprint π(r) is randomized with some or each selection of input image u. Deterministic or random, preferably the placement is constrained by medical or anatomical constraints. For example, the balloon catheter footprint cannot be placed at a position where there is no blood vessel footprint, etc. Much rather, the balloon catheter footprint should preferably be aligned with and superimposed on a section of a blood vessel footprint.

As a result of step S830, a predefined fraction (or all image specimens) in the augmented training data set u'∈U' now include (or do not include) such a projection footprint. This fraction is larger than before augmentation. The fraction may be 50%, or other. The fraction may be user adjustable by a suitable user interface. The new data set U' is more variable with respect to certain image structures (for example said projection footprint) caused by a given context or combination of contexts, as compared to unmodified original data. Thus, the unfavorable bias or deficiency of variability of such image structures has been compensated for by the proposed modifier step S830.

At step S840 the so modified image is then associated with the corresponding label P of the original image u, selected at said step S810 as the input image for the modification operation. Alternatively, a new label P' is generated for modified image u' based on the very modification. For example, for localization tasks, where the to be trained system is to localize the device footprint in the image, the location, orientation, bounding box etc of the synthesized footprint automatically yield the new label P'. The method may thus support automatic labelling of an enlarged training data set.

At an optional step S850, the modified image with its label P associated may then be stored in the training data set U to obtain the augmented or modified or prepared data stet U'. The modified image u' can be stored alongside unmodified ones in the original storage MEM-TD, or may be stored separately from the unmodified image specimens in a separate memory/storage.

The previously described steps S810-S850 may be repeated until a sufficient number of training images have been modified. Plural such modified images may be generated in this manner. In particular, the steps S810-S850 are repeated until all images earmarked for selection by selector SL have been processed. The number of images to be modified may also be randomized or may be determined by the user by specifying a certain fraction of modified images that are required to improve the existing training data set. As such, once one or more or the requisite number of modified images have been generated as described above, the training data preparation or augmentation phase terminates and process flow may proceed to the machine learning phase.

Specifically, at an optional step S860, a machine learning algorithm is using the modified images, optionally in combination with the original, unmodified images that did not need modification. The original images u that did need modification and that have been modified into respective modified images u' are as such no longer required and may no longer form part of the (new) training data set U'. However, so as to increase the variance of the new data set as whole, it may be preferred to retain the original imagery pre-modification, together with their modified specimen counterparts. In other words, a selection (such as the mini-batch) of data from new set U' may contain unmodified specimens, modified specimens, and unmodified specimens from which however modified specimens were derived. Thus, as preferably envisaged herein, the new data set U' is not merely enlarged but the image content is now more variable, with less bias. It is also contemplated herein to modify specimens multiple times. For example, multiple footprints of multiple devices may be included. For example, footprints of a balloon catheter and a TEE probe may both blended into a given image specimen.

Using in step S860 the modified images may include, for model-based approaches, training, by a machine learning algorithm, an ML model. The training is based in particular on the new training data set U'. Training may include adjusting, based on the new training data set U', parameters of the machine learning. The model may include initially an initial set of parameters which is then adapted to improve an objective function F, such as a cost or utility function. The adjusting of the parameters may be gradient-based, such as forward-backward propagation techniques as may be used for training neural network type models. When using non-model based, "free", ML-algorithms, the new training data set U' is used at step S860 to (directly) compute, based on the machine learning algorithm, such as k-nearest neighbors or other clustering techniques, the sought after result RS.

Prior to using the modified images in step S860, the modified images may be added to a training batch. Whether or not the modified image is selected for being so added may also be randomized. In other words, when compiling a training batch, a sub-selection from set U' is defined. This sub-selection may include training images that are modified ones, whilst others are unmodified ones, not processed by the modifier system TDM.

As mentioned earlier, the modification operation at step S830 may be interleaved with training step S860. In other words, modification proceeds batch-wise, which is followed by one or more cycles of training. Then, a new training-batch is drawing from the currently updated new set U' of training data including the modified and unmodified data. A mini-batch stochastic gradient descent algorithm, or similar variations may be used as an optimization method for adjusting the parameters.

Alternatively, the steps S810-S850, in particular modifier step S830, may all be completed in a preparatory phase prior to the training step S860. In other words, all the modification operations for a certain fraction of image u are first concluded to build up the new set U, and only then is training step S860 started, based on new set U'. Preferably, batch-wise training is used but this may not be necessary in all embodiments.

As mentioned, in some embodiments the training model is a neural network model, such as a convolutional model CNN or other neural network models such as fully connected neural network model. The neural network model may be partly or wholly recurrent or partly or wholly feedforward. Non-neural network type models are also envisaged herein, such as support vector machines (SVM), k-nearest neighbors methodology, decision trees, random forest, multivariate regression (weighted linear or logistic regression). Still other techniques may include Bayesian networks, or random fields, such as Markov type random field and others still that are based on training data.

Figure 9:
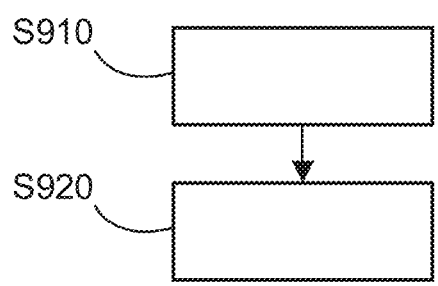
FIG. 9 shows a flow chart of a machine learning algorithm that uses training data.

Once the model has been sufficiently trained this may then be made available for deployment as shown in inset flow chart FIG. 9.

At step S910, an input image is acquired during deployment, like in everyday clinical practice or during testing phase. Specifically, the input image is not from the training data set U'.

The input image is processed at step S920 by using the model to produce the ML result RS, which can then be displayed, stored or otherwise further processed. Specifically, The model is applied to the input data to produce the result RS, such as classification or regression result. A model however may not necessarily be required, as in some clustering algorithms where the (now enlarged) training data set U' is used directly to compute the result, for example by finding the k-closest neighbors in clustering, etc.

As mentioned earlier, the modification operation step S830 may be randomized or deterministic. In either case, the modification operation step S830 is preferably constrained by prior knowledge, such as anatomical or medical knowledge as mentioned earlier in connection with placement of the balloon catheter footprint, consistent with the geometry of the blood vessels as recorded in the image u to be modified. In other intervention types, there may be other anatomical constraints to consider.

The manner in which the said constraints on modification operate may depend on the above mentioned contexts.

Specifically, in relation to the procedure context, interventional devices BC may behave differently in various states of deployment. For instance, a mitral clip can be closed, opened, or deployed. In order to account for such changes, the random generator not only chooses the position and orientation of the device model from set R, but also specifies a device model's state or configuration. In another example, the modification operation S830 may augment the X-ray images by combining the imagery u with a projection footprint of an endograft that is deployed using a sheath, eventually withdrawn. In this case, the model of the device is determined by length of sheath withdrawal and potentially information about the patient anatomy. Generally, a device state may relate to changeable shape of the medical device. As another example, the balloon catheter BC may be capable of assuming multiple two states, such as deflated/inflated state, as shown in inset FIG. 2A, B. Similarly, there may be an open and closed state of a mitral valve clip, and so on for other tools, devices or implements as may be used in the intervention as mentioned above in relation to FIG. 7.

In yet another embodiment, modifying step S830 is based on device-specific information, such as mechanical properties, material, typical deployment parameters (pressure, imaging angles), as well as tissue properties typically surrounding the device. For instance, shape and dimensions of the balloon catheter is not only influenced by applied pressure, but it also conforms to the vessel's anatomy. By taking into account surrounding anatomies and properties of the devices, whose projection footprint is to be combined with the input imagery, a more realistic modified imagery u' can be obtained, Thus, in embodiments, the step S830 of modifying the input image by combining the input image with a device BC's projection footprint may include a sub-step of ascertain first the anatomy captured in the image, and take the anatomy into account when placing and/or orienting the device's footprint. Specifically, the step of modifying S830 may include a pre-processing step of segmenting first the input image u for existing anatomical structures $S_i$ and/or other devices $D_i$ in the (possibly randomly) selected image u. Optionally, orientation of the anatomical structure/device is identified.

For a given device projection footprint to be artificially combined into the image, a set of rules for each $S_i$, $D_i$ may be applied to determine allowed and/or prohibited relative positioning and/or orientation between the existing structures $S_i$ and devices $D_i$ and the device to be introduced artificially. The rules are to constrain the modifying operation S830, based on medical knowledge. The rules can be specified empirically or can be learned from segmentations of images with segmented devices. Examples for such rule may be formulated for in-vessel devices, such as balloons, catheters and guidewires that run inside blood vessels and are oriented in the vessel direction, not at a (significant) angle to the vessels. For example, a balloon is always inside a vessel, so its footprint cannot be placed outside the vessel footprint and no part may extend beyond vessel footprint, etc. Another rule may be formulated as follows: balloons may be inflated in the coronaries running largely parallel to the surface, outside the heart—not inside the heart. Another rule may read: "valve clips and artificial valves are deployed inside the heart, not outside".

Thus, the localization of the modification S830 is preferably (also) randomized, but is preferably constrained by prior knowledge. For example, the balloon footprint may be placed anywhere in the image, so long as such placement is consistent given anatomical constraints and/or temporal constraints. Again, a suitably rule-constrained random number generator may be use to sample the image plane for placement of the modified structure, such as a device projection footprint. Pose or orientation of the model which is to be projected may also be randomized, but again, preferably, with due regard to applicable anatomical constraints.

As to the patient context, many minimally invasive X-ray based procedures, such as the above mentioned percutaneous coronary interventions, are performed under cardiac and respiratory motion. In this embodiment, such motion is taken into account in the modifying step S830. Not only state and/or position/orientation of the device in respect to the anatomy may be taken into account, but in addition the patient motion. This may be implemented by randomizing one more of respiratory and cardiac motion. In addition or instead, The randomization may include randomizing any one or more of patient position and orientation, soft tissue deformation, as well as information from a navigation system (e.g. device-to-image registration), if available. In other words, such prior-knowledge-constraint embodiments of augmentation at step S830, additional temporal and/or motion components are added to the standard placement of the device footprint. For instance, guidewires typically move forward not side-to-side during navigation. As a another example, an end effector for delivery of a mitraclip has a defined steerability characteristic, so by virtue of its design, there are only a finite number of configurations that the device may assume. Other such kinematic or mechanical constraints can be taken into account for other devices. The same principles may be applied to internal devices, such as implants in patent context.

With continued reference to the modification operation at step S830, the combining of imagery with projection footprints is not confined to the procedure context discussed above.

A similar approach may be used in order to account for image structures in the imaging context. Some such structures may be caused by imaging parameters, for example collimator settings. Natively un-collimated or differently collimated input images may be modified by combining with collimator blade footprints at different positions or openings. Such synthetic collimator blade structures may be superimposed using the above described ray casting approaches, with a model for the imaging equipment (such as the collimator blade), instead of the model for the medical device or tool. Such blades have a known radiation opacity and thus the shadow pixel values that the blades induce are known. In addition to changes in collimation, changes in magnification can be modelled by ray-casting with variation of distance between the virtual/conceptual image plane and source position X.

In patient context, structures caused by implants that are resident in the imaged patient from the start may also be compensated for by projection footprint based modification, given mesh models for such implants.

However, the modification operation as described above at step S830 may not necessarily include combining a projection footprint with natively recorded imagery. Other manners of modification are also envisaged herein in other contexts. For example, in patient context, image structures representative of certain medical abnormalities may be included into the imagery u to be modified, such as fractures or tumor growths or similar. This may be done by registration and morphing technique. In the input image u, bone structures are identified at step S830. The structures are registered broadly with an auxiliary image of a fractured bone. The bone structure in image u is then morphed towards the structure representative of the fractured bone in the auxiliary image, to so generate synthetically a modified training image u', now representing fractured bone portion, whilst the input image u had represented an uncompromised bone portion. Conversely, image structures for fractured bones may be morphed "back" into structures representative of an uncompromised, healthy bones. Other lesions can be artificially introduced in this manner into the imagery u to be modified, such as malformation or damages in vessels.

Most of the modification operation so far as described for step S830 are configured to cause local modifications in the input image u. However, other modification operations are also envisaged that cause global changes to the input image u. Such globally acting modifications may be thought of as simulation operations. For example, in the imaging context, in order to simulate variations of the tube voltage and/or amperage that influence the energy of the X-ray beam, known X-ray simulation algorithms or Monte-Carlo (MC) simulation techniques may be used to transform input image u acquired at a given energy to an approximation of the same image at a different energy. For example, Monte-Carlo simulation techniques may be used to simulate X-rays having specific properties. For example, some such algorithms use Poisson distributions for generating x-ray spectra, and can simulate material interactions, scattering etc and detection and scintillation on a given detector specification. Similar simulation system have been described by Luzhen Deng et al in "*A Geant4-based Monte Carlo study of a benchtop multi-pinhole X-ray fluorescence computed tomography imaging*", published in *Int J Nanomedicine*, Vol. November 8; 13, pp 7207-7216 (2018). Such MC based techniques may be used to simulate other hardware settings, such as detector gains, filtering options and other. See for example Daniel A. B. Bonifácio et al, "*Monte Carlo simulation of X-ray spectra in diagnostic radiology and mammography using Geant4*", published as a conference paper, "International Nuclear Atlantic Conference—INAC 2005", Santos, SP, Brazil, Aug. 28 to Sep. 2, 2005, ASSOCIAÇÃO BRASILEIRA DE ENERGIA NUCLEAR (ABEN), ISBN: 85-99141-01-5.

Monte-Carlo-based techniques may also be used to simulate different scattering contributions. This may be relevant when accounting for different scatter levels caused by patients having different BMI-indices for example. This may allow compensating a bias in the training data set caused by a high proportion of images from patients in a given BMI-index range.

In embodiments, spectral imaging techniques or spectral imaging algorithms may be used, such as described by R. E. Alvares et al in their 1976 paper "*Energy-selective reconstructions in X-ray computerized tomography*", published in Phys. Med. Biol., vol 21(5), pp 733-44. Preferably for this embodiment, the original training data set has been acquired by a spectral imaging apparatus such as dual source imager or an imager with a multi-layer detector, or an imager with a photon-counting detector etc. Such imagers generate spectral data from which the modified images u' at different X-ray energy can be simulated and computed.

In addition to or instead of using analytical computational methods as described above, the modification operation step S830 may be implemented itself by ML-techniques. For example, neural networks of the generative type, such as GANs ("Generative Adversarial Networks") first proposed by I. Goodfellow et al in 2014 (available online at arXiv: 1406.266) may be configured to implement any of the above described modification operations. GANs may be used and trained to generate artificial X-ray images u' that include, for example, the required projection footprints of devices of interest, although the input image u fed into the GAN did not include such structures. Preferably, such generative ML models (such as GAN) may be used to remove structures. Alternatively or additionally, such generative ML-setups may be used to stimulate different X-ray source settings and thus imagery as if acquired with such settings.

Whilst most of the above-described embodiments of the modifying operation S830 acts in the spatial domain, this is not a requirement herein. Alternative embodiments may first transform the input image u into frequency domain, perform the modifying operation there, and transform back into spatial domain to so generate the modified image u'.

The components of system TDM may be implemented as one or more software modules, run on one or more general-purpose processing units PU such as a workstation associated with the imager IA, or on a server computer associated with a group of imagers.

Alternatively, some or all components of the system TDM may be arranged in hardware such as a suitably programmed microcontroller or microprocessor, such an FPGA (field-programmable-gate-array) or as a hardwired IC chip, an application specific integrated circuitry (ASIC), integrated into the imaging system IA. In a further embodiment still, any one of systems TS, SYS may be implemented in both, partly in software and partly in hardware.

The different components of any one or system TDM may be implemented on a single data processing unit PU. Alternatively, some or more components are implemented on different processing units PU, possibly remotely arranged in a distributed architecture and connectable in a suitable communication network such as in a cloud setting or client-server setup, etc.

One or more features described herein can be configured or implemented as or with circuitry encoded within a computer-readable medium, and/or combinations thereof. Circuitry may include discrete and/or integrated circuitry, a system-on-a-chip (SOC), and combinations thereof, a machine, a computer system, a processor and memory, a computer program.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A system for providing medical training data for a machine learning model, the system comprising:
   a processor in communication with memory, the processor configured to:
      obtain the medical training data including medical training imagery of an anatomy of one or more patients,
      compute a projection footprint of a model representative of a medical object associated with a medical procedure,
      access a set of rules corresponding to the model, wherein the set of rules defines determining a location to position the model within the anatomy with respect to one or more structures that represents a realistic positioning of the medical object with respect to the one or more structures for the medical procedure, and
      modify the medical training imagery by positioning the projection footprint in the medical training imagery based on the set of rules.

2. The system of claim 1, wherein the medical object comprises one of i) a medical tool for a medical procedure, ii) an equipment of a medical imaging apparatus, or ii) an anatomical structure of a patient or part thereof.

3. The system of claim 1, wherein the one or more structures relates to an acquisition operation of a medical imaging apparatus, and the processor is configured to determine the acquisition operation based on one or more imaging parameters for radiation generation by the medical imaging apparatus.

4. The system of claim 1, wherein the processor is configured to modify the medical training imagery randomly or deterministically.

5. The system of claim 1, wherein the set of rules comprise constraints on modification to the medical training imagery based on prior anatomical knowledge that pertains to at least one of i) the anatomy of the one or more patients, ii) one or more devices inserted into the one or more patients, and iii) a medical procedure performed on the one or more patients.

6. The system of claim 1, wherein the set of rules comprise temporal constraints on modification to the medical training imagery, the temporal constraints pertaining to at least one of i) the anatomy of the one or more patients, ii) one or more devices inserted into the one or more patients, and iii) a medical procedure performed on the one or more patients.

7. The system of claim 1, wherein the processor is configured to adjust one or more parameters of the machine learning model based at least on the modified medical training imagery.

8. The system of claim 7, further comprising at least one of volatile memory and non-volatile memory, and wherein the processor is configured to store the machine learning model and the modified medical training imagery in the at least one of the volatile memory and non-volatile memory.

9. The system of claim 7, wherein the processor is further configured to:
obtain input medical imagery from a medical imaging apparatus; and
apply the input medical imagery to i) the trained machine learning model or ii) training data including the modified medical training imagery to obtain a medical machine learning result.

10. A method of providing medical training data for a machine learning model, the method comprising:
obtaining the medical training data including medical training imagery of one or more patients;
computing a projection footprint of a model representative of a medical object associated with a medical procedure;
accessing a set of rules corresponding to the model, wherein the set of rules defines determining a location to position the model within anatomy with respect to one or more structures that represents a realistic positioning of the medical object with respect to the one or more structures for the medical procedure; and
modifying the medical training imagery by positioning the projection footprint in the medical training imagery based on the set of rules.

11. The method of claim 10, further comprising:
obtaining input medical imagery from a medical imaging apparatus;
applying the input medical imagery to i) the trained machine learning model or ii) training data including the modified medical training imagery to obtain a medical machine learning result.

12. The method of claim 10, wherein the one or more structures relates to an acquisition operation of a medical imaging apparatus, and the method further comprises determining the acquisition operation based on one or more imaging parameters for radiation generation by the medical imaging apparatus.

13. The method of claim 10, wherein the set of rules comprise constraints on modification to the medical training imagery based on prior anatomical knowledge that pertains to at least one of i) the anatomy of the one or more patients, ii) one or more devices inserted into the one or more patients, and iii) a medical procedure performed on the one or more patients.

14. The method of claim 10, wherein the set of rules comprise temporal constraints on modification to the medical training imagery, the temporal constraints pertaining to at least one of i) the anatomy of the one or more patients, ii) one or more devices inserted into the one or more patients, and iii) a medical procedure performed on the one or more patients.

15. The method of claim 10, further comprising adjusting one or more parameters of the machine learning model based at least on the modified medical training imagery.

16. A non-transitory computer readable storage medium having stored a computer program comprising instruction which, when executed by a processor, cause the processor to:
obtain medical training data including medical training imagery of an anatomy of one or more patients;
compute a projection footprint of a model representative of a medical object associated with a medical procedure;
access a set of rules corresponding to the model, wherein the set of rules defines determining a location to position the model within the anatomy with respect to one or more structures that represents a realistic positioning of the medical object with respect to the one or more structures for the medical procedure; and
modify the medical training imagery by positioning the projection footprint in the medical training imagery based on the set of rules.

17. The non-transitory computer readable storage medium of claim 16, wherein the one or more structures relates to an acquisition operation of a medical imaging apparatus, and the instructions, when executed by the processor, further cause the processor to determine the acquisition operation based on one or more imaging parameters for radiation generation by the medical imaging apparatus.

18. The non-transitory computer readable storage medium of claim 16, wherein the set of rules comprise constraints on modification to the medical training imagery based on prior anatomical knowledge that pertains to at least one of i) the anatomy of the one or more patients, ii) one or more devices inserted into the one or more patients, and iii) a medical procedure performed on the one or more patients.

19. The non-transitory computer readable storage medium of claim 16, wherein the set of rules comprise temporal constraints on modification to the medical training imagery, the temporal constraints pertaining to at least one of i) the anatomy of the one or more patients, ii) one or more devices inserted into the one or more patients, and iii) a medical procedure performed on the one or more patients.

20. The non-transitory computer readable storage medium of claim 16, wherein the instructions, when executed by the processor, further cause the processor to adjust one or more parameters of a machine learning model based at least on the modified medical training imagery.

* * * * *